United States Patent
Hortin et al.

(10) Patent No.: US 11,458,082 B1
(45) Date of Patent: Oct. 4, 2022

(54) TANNING COMPOSITIONS INCLUDING DIHYDROXYACETONE

(71) Applicant: Curb Appeal Beauty LLC, Lehi, UT (US)

(72) Inventors: Christi Martino Hortin, Lehi, UT (US); Tesla Ann Welch, Lehi, UT (US); Arthur C. W. Georgalas, Warwick, NY (US); Bruce W. Gesslein, Brick, NJ (US); Irwin Palefsky, West Orange, NJ (US)

(73) Assignee: Curb Appeal Beauty LLC, Lehi, UT (US)

( * ) Notice: Subject to any disclaimer, the term of this patent is extended or adjusted under 35 U.S.C. 154(b) by 0 days.

(21) Appl. No.: 16/657,381

(22) Filed: Oct. 18, 2019

Related U.S. Application Data

(60) Provisional application No. 62/747,308, filed on Oct. 18, 2018.

(51) Int. Cl.

| | |
|---|---|
| *A61K 8/38* | (2006.01) |
| *A61K 8/02* | (2006.01) |
| *A61K 8/06* | (2006.01) |
| *A61K 8/34* | (2006.01) |
| *A61K 8/49* | (2006.01) |
| *A61K 8/92* | (2006.01) |
| *A61Q 17/04* | (2006.01) |
| *A61K 8/35* | (2006.01) |

(52) U.S. Cl.
CPC .............. *A61K 8/35* (2013.01); *A61K 8/0229* (2013.01); *A61K 8/064* (2013.01); *A61K 8/345* (2013.01); *A61K 8/4973* (2013.01); *A61K 8/92* (2013.01); *A61Q 17/04* (2013.01); *A61K 2800/524* (2013.01)

(58) Field of Classification Search
CPC .......... A61K 8/35; A61K 8/92; A61K 8/4973; A61K 8/345; A61K 8/064; A61K 8/0229; A61K 2800/524; A61Q 17/04
See application file for complete search history.

(56) References Cited

U.S. PATENT DOCUMENTS

| | | | |
|---|---|---|---|
| 6,630,130 B1 * | 10/2003 | Grimes | A61K 8/35 424/59 |
| 2007/0003496 A1 * | 1/2007 | Dueva-Koganov | A61Q 19/04 424/59 |
| 2009/0317342 A1 * | 12/2009 | Rudolph | A61Q 19/04 424/59 |

OTHER PUBLICATIONS

Epstein, "DHA Stability Evaluations", Feb. 28, 2012, 6 pages.

* cited by examiner

*Primary Examiner* — Trevor Love
(74) *Attorney, Agent, or Firm* — Dorsey & Whitney LLP

(57) ABSTRACT

Embodiments disclosed relate to self-tanning compositions that include at least 0.1 weight percent dihydroxyacetone and at least 1 weight percent water in an internal phase in addition to an external phase formulated to provide a solid body, and the self-tanning composition is stable at ambient temperatures.

14 Claims, 1 Drawing Sheet

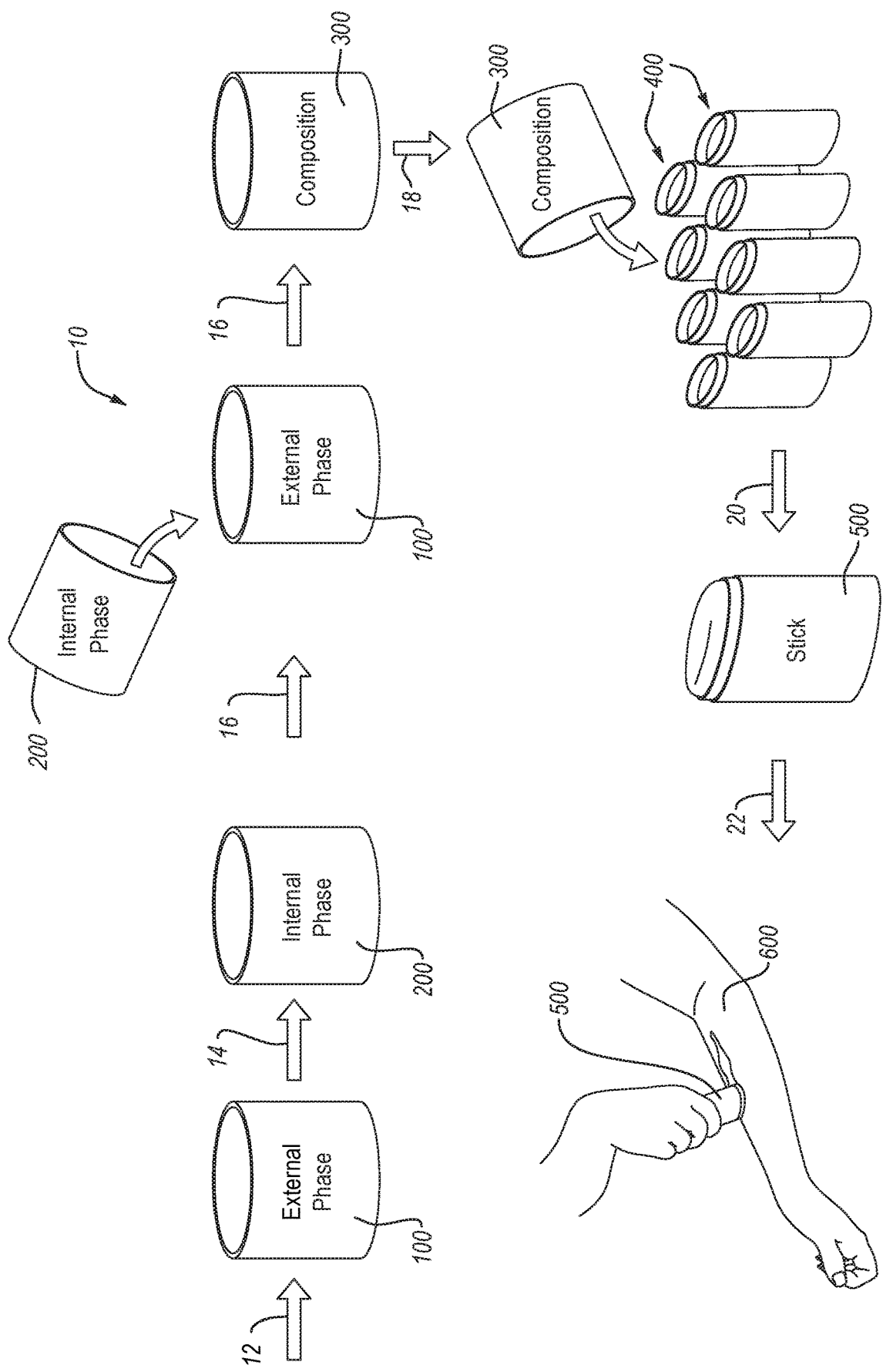

TANNING COMPOSITIONS INCLUDING DIHYDROXYACETONE

CROSS-REFERENCE TO RELATED APPLICATIONS

This application claims priority to U.S. Application No. 62/747,308 filed on 18 Oct. 2018, the disclosure of which is incorporated herein, in its entirety, by this reference.

BACKGROUND

Self-tanners are typically sprays, lotions, or other fluid compositions that contain a tanning agent. The tanning agent may be difficult to maintain in a stable form or may require solvents such as low molecular weight alcohols.

SUMMARY

Embodiments disclosed herein relate to self-tanning compositions that are stable in solid form and contain at least 0.1 weight % ("wt %") dihydroxyacetone ("DHA") and at least 1 wt % water and methods of forming such self-tanning compositions.

In an embodiment, a self-tanning composition is disclosed. The self-tanning composition includes a solid body including a water in oil emulsion. The water in oil emulsion includes an external phase including a plurality of components. The water in oil emulsion includes an internal phase including water and dihydroxyacetone. The water is at least 1 wt % of the water in oil emulsion, dihydroxyacetone is at least 0.1 wt % of the water in oil emulsion, and the solid body is stable at ambient temperatures.

In an embodiment, a method of forming a self-tanning composition is disclosed. The method includes forming at least one external phase. The method includes forming at least one internal phase. The method includes combining the at least one external phase with the at least one internal phase to form a self-tanning composition. The method includes cooling the self-tanning composition to form a self-tanning stick. The self-tanning composition formed from the method includes at least 0.1 wt % DHA and at least 1 wt % water in the internal phase.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical or similar elements or features in different views or embodiments shown in the drawings.

FIG. 1 is a schematic of a method of making and using a solid self-tanning composition containing DHA.

DETAILED DESCRIPTION

Embodiments disclosed herein relate to self-tanning compositions which contain dihydroxyacetone (hereinafter "DHA") and are stable in solid form at ambient temperatures. The self-tanning compositions include an emulsion having an internal phase and an external phase (e.g., continuous phase). The external phase includes oily or waxy components and the internal phase includes a solvent mixture containing the DHA as a solute therein. The DHA is present in the internal phase in monomer form, which is more easily delivered and bound to the amino groups of skin cells. Water-in-oil (e.g., invert) emulsions are disclosed herein, wherein the internal water phase contains and protects DHA and the external oil phase is formulated to provide structural stability to the composition at ambient temperatures (or temperatures below 60° C.) and other effects such as skin penetration and emollient properties, all while maintaining the water phase as an internal component. The self-tanning compositions may be provided in a solid form having a viscosity that allows the body of the self-tanning composition to remain intact and in a predetermined shape under ambient conditions. While the term "solid" is used herein, the term "solid" may include a colloid of the solid external phase and the liquid internal phase which may form a solid emulsion, a gel, or a film. The "solids" disclosed herein support their own weight and maintain a selected shape but may flow (albeit slowly) under applied pressure. Accordingly, the solid self-tanning compositions disclosed herein may include a viscoelastic solid or an amorphous solid. The solids disclosed herein may have a consistency and viscosity akin to petroleum jelly, a deodorant stick, or the like. The solid self-tanning compositions disclosed herein may have a density at ambient temperatures of at least 0.1 g/cm$^3$, such as greater than 0.5 g/cm$^3$, 0.5 g/cm$^3$ to 2 g/cm$^3$, 0.75 g/cm$^3$ to 1.4 g/cm$^3$, 0.85 g/cm$^3$ to 1.3 g/cm$^3$, 0.75 g/cm$^3$ to 0.9 g/cm$^3$, 0.9 g/cm$^3$ to 1.1 g/cm$^3$, 1.1 g/cm$^3$ to 1.3 g/cm$^3$, or less than 2 g/cm$^3$.

As used herein, "dihydroxyacetone" or "DHA" may include one or more of the dimer species (2,5-bis(hydroxymethyl)-1,4-dioxane-2,5-diol), the monomer species, or derivatives thereof (e.g., reaction products or intermediates), as context dictates. For example, when discussing DHA powder, one having ordinary skill in the art will understand that the DHA is present in the dimer form, and when discussing DHA in solution, one having ordinary skill in the art will understand that the DHA is present in the monomer form, derivatives thereof, or intermediates between the monomer and dimer forms.

The monomer form of DHA, which operates as an active molecule (e.g., reagent) when in contact with amino groups of skin cells, is particularly difficult to encapsulate in a solid, deliverable form. Monomer DHA typically deactivates in solutions with a pH above 7.0. Further, DHA may provide a different hue to skin at when present in solution with various pHs. For example, as the pH of the solution carrying DHA approaches 7.0, the resulting color provided to skin where the DHA is applied appears more orange than brown. The present disclosure provides solid, stable DHA-containing compositions suitable for providing a self-tanning effect on human skin, at a selected pH.

The external phase of a DHA-containing composition may contain one or more waxes, gellants, emollients, emulsifiers, skin penetration enhancers, or other components. The external phase and one or more components therein may be a wax or oil, or may be substantially waxy or oily when melted (e.g., at temperatures above 70° C.). For example, the external phase may include one or more of synthetic wax (e.g., polyethylene), *Euphorbia Cerifera* (candelilla) wax, ozokerite (paraffin), and emollients and emulsifiers such as neopentyl glycol diethylhexanoate ([3-(2-ethylhexanoyloxy)-2,2-dimethylpropyl] 2-ethylhexanoate), isononyl isononanoate (3,5,5-trimethylhexyl 3,5,5-trimethylhexanoate), isosorbide dicaprylate ([(3S,3aR,6R,6aR)-6-octanoyloxy-2,3,3a,5,6,6a-hexahydrofuro [3,2-b]furan-3-yl] octanoate), dimethicone (dimethyl-bis(trimethylsilyloxy)silane), diemethicone/polyglicerine-3 crosspolymer dimethicone, PEG-9 polydimethylsiloxyethyl dimethicone, cyclomethicone (cyclopentasiloxane or cyclohexasiloxane), cyclohexasiloxane, L-Bisabolol, dibutyl lauroyl glutamide ((2S)—N,N'-dibutyl-2-(dodecanoylamino) pentanediamide), dibutyl ethylhexanoyl glutamide ((2S)—N,N'-dibutyl-2-(2-ethylhexanoylamino)pentanediamide), sorbitan oleate ([(2R)-2-[(3R,4S)-3,4-dihydroxyoxolan-2-yl]-2-hydroxyethyl] (Z)-octadec-9-enoate), polysorbate 80 (polyoxyethylene (20) sorbitan monooleate), hydroxystearic acid (12-hydroxyoctadecanoic acid), polyhydroxystearic acid (e.g., Kester Wax K-60p), vitamin E acetate (e.g., dl-alpha-tocopheryl acetate or [(2R)-2,5,7,8-Tetramethyl-2-[(4R,8R)-4,8,12-trimethyltridecyl]chroman-6-yl] acetate), chamomile abstract such as *Chamomilla Recutita* (*Matricaria*) Flower Extract (e.g., actiphyte of chamomile), isodecyl neopentanoate (decyl 2,2-dimethylpropanoate), isohexadecane (2,2,4,4,6,6,8-heptamethylnonane), any wax or waxes, emollients, emulsifiers, or the like. The weight percentages of each external phase component (relative to the total weight of the DHA-containing composition) may vary as disclosed in more detail below.

One or more of the external phase components may be waxy or oily and form a solid body at room temperature or higher (e.g., below above 50° C. or 60° C.). Any of the external phase components may be provided in powder, pellet, bar, ingot, fluid, etc., form. In some cases it may be necessary to heat one or more of the external phase components to place said components into a liquid phase. The melting temperature of the external phase (as determined by the component with the highest melting point) may be at least 50° C., such as 50° C. to 135° C., 50° C. to 80° C., 60° C. to 90° C., 70° C. to 90° C., 80° C. to 90° C., 80° C. to 100° C., 100° C. to 135° C., at least 60° C., at least 70° C., at least 80° C., at least 100° C., less than 150° C., less than 135° C., less than 120° C., or less than 120° C. At the melting temperature of the external phase, the external phase may be a fluid mixture with substantially no solids.

In some examples, the external phase may be provided as a single mixture of components or more than one mixture (e.g., at least two, three, four, etc., mixtures) of components. The external phase may be combined with the internal phase in a selected ratio of external phase to internal phase (by weight).

As discussed in more detail below, individual components of the external phase of the self-tanning compositions may be present in the external phase in an amount of at least 0.1 weight percent (wt %) of the self-tanning composition, such as 0.1 wt % to 50 wt %, 0.25 wt % to 25 wt %, 20 wt % to 50 wt %, 0.5 wt % to 20 wt %, 1 wt % to 10 wt %, 5 wt % to 10 wt %, 5 wt % to 15 wt %, 15 wt % to 25 wt %, 0.25 wt % to 2.0 wt %, 0.5 wt % to 1 wt %, 4 wt % to 10 wt %, 4 wt % to 8 wt %, 3 wt % to 8 wt %, 2 wt % to 8 wt %, 1 wt % to 4 wt %, 1 wt % to 3 wt %, 2 wt % to 5 wt %, 0.5 wt % to 3 wt %, less than 50 wt %, less than 25 wt %, or less than 10 wt % of the self-tanning composition.

The pH of the external phase may be substantially neutral, such as between 6 pH and 7.5 pH, 6 pH and 6.8 pH, 6.5 pH and 7.5 pH, 6.5 pH and 7.2 pH, or 6.8 pH and 7.1 pH. Due to the substantially anhydrous characteristics of the external phase, the external phase may not have a meaningful pH. For example, the pH of the external phase, while substantially neutral, may not have enough aqueous material therein to effect the pH of the internal phase when in contact therewith. Accordingly, the external phase components may not react with or degrade the internal phase components an any appreciable amount.

The internal phase of a DHA-containing composition may contain one or more solvents, preservatives, skin penetration enhancers, DHA color modifiers or enhancers, humectants, moisturizers, or colorants (e.g., DHA). The internal phase and one or more components therein may be solvents or solutes in the solvent(s). The one or more solvents may include a primary solvent such as water (e.g., deionized water), one or more glycols (e.g., propylene glycol, or other glycol ethers), or the like. For example, the internal phase may include one or more of water, one or more glycols, one or more preservatives (e.g., phenoxyethanol, ethylhexyglycerin, propylene glycols, polyethylene glycols, parabens, or the like), dimethyl isosorbide, erythrulose ((R)-1,3,4-trihydroxybutan-2-one), glycerin, DHA, plant extracts (e.g., aloe vera extract), or other components. The components of the internal phase do not deactivate DHA. That is, the components of the internal phase do not react with DHA to convert the DHA to a non-reactive derivative or back-convert the monomeric DHA to the dimer form.

Any of the internal phase components may be provided in powder, pellet, bar, ingot, fluid, etc., form. In some cases it may be necessary to heat one or more of the internal phase components to place said components into a liquid phase. The melting temperature of the internal phase (as determined by the component with the highest melting point) may be at least 50° C., such as 50° C. to 135° C., 50° C. to 80° C., 60° C. to 90° C., 70° C. to 90° C., 80° C. to 90° C., 80° C. to 100° C., 100° C. to 135° C., at least 60° C., at least 70° C., at least 80° C., at least 100° C., less than 150° C., less than 135° C., less than 120° C., or less than 120° C. At the melting temperature of the internal phase, the internal phase may be a fluid (e.g., solvent) mixture with substantially no solids therein. After cooling, one or more of the internal phase components may be in liquid or solid form.

While most components of the compositions disclosed herein are provided in the International Nomenclature of Cosmetic Ingredients ("INCI") format, the International Union of Pure and Applied Chemistry ("IUPAC") naming formats are also or alternatively provided in parenthetical form when applicable. In some examples, the IUPAC name is provided instead of the INCI name, as is apparent from context. In some examples, the common name or trade name of the components are provided.

As discussed in more detail below, individual components of the internal phase of the self-tanning compositions may be present in the internal phase in an amount of at least 0.1 wt % of the self-tanning composition, such as 0.1 wt % to 50 wt %, 0.25 wt % to 25 wt %, 20 wt % to 50 wt %, 0.5 wt % to 20 wt %, 1 wt % to 20 wt %, 1 wt % to 10 wt %, 5 wt % to 10 wt %, 5 wt % to 15 wt %, 15 wt % to 25 wt %, 0.25 wt % to 2.0 wt %, 0.5 wt % to 1 wt %, 4 wt % to 10 wt %, 4 wt % to 8 wt %, 3 wt % to 8 wt %, 2 wt % to 8 wt %, 1 wt % to 4 wt %, 1 wt % to 3 wt %, 2 wt % to 5 wt %, 0.5 wt % to 3 wt %, less than 50 wt %, less than 25 wt %, or less than 10 wt % of the self-tanning composition. In some examples, the DHA may be present in the internal phase in an amount that is at least 0.1 wt %, such as 0.1 wt % to 99 wt %, 1 wt % to 20 wt %, 1 wt % to 10 wt %, 5 wt % to 20 wt %, 5 wt % to 15 wt %, 5 wt % to 10 wt %, less than 20 wt %, less than 10 wt %, or less than 5 wt %. The water content (or other solvent such as propylene glycol) in the internal phase may be at least 1 wt %, such as 1 wt % to 50 wt %, 1 wt % to 10 wt %, 5 wt % to 15 wt %, 8 wt % to 15 wt %, 10 wt % to 20 wt %, 15 wt % to 25 wt %, 20 wt % to 50 wt %, 30 wt % to 40 wt %, or less than 50 wt %, so long as the DHA is dissolved therein. The inventors have found the self-tanning compositions disclosed herein provide particularly satisfactory self-tanning effect (e.g., resulting color on skin) at a solvent (e.g., water) content of at least 9 wt % of the self-tanning composition (or internal phase), such as 9 wt % to 50 wt %, 20 wt % to 50 wt %, 25 wt % to 35 wt %, 30 wt % to 40 wt %, 35 wt % to 40 wt %, or less than 40 wt %.

The pH of the internal phase may be greater than 3, such as 3 pH to 7.5 pH, 3 pH to 7 pH, 5 pH to 7 pH, 5 pH to 6.5 pH, 5 pH to 6 pH, 5 pH to 5.5 pH, 5.5 pH to 6.5 pH, 6 pH and 7 pH, less than 7 pH, less than 6 pH, or less than 5 pH. As noted above, by selectively controlling the pH of the internal phase, the final hue of the as-applied self-tanning composition can be selectively controlled. For example, as the pH of the internal phase (or the entire self-tanning composition) approaches 7.0, the self-tanning compositions herein provide a more orange hue, whereas when the pH is between 5 and 5.5, the self-tanning compositions herein provide a more brown hue. Accordingly, the color of the as-applied self-tanning compositions disclosed herein can be selectively controlled by controlling the components of the internal phase or entire self-tanning composition to provide a selected pH.

In some examples, one or more of the internal phase or the external phase may include one or more optional components, such as scents (e.g., esters) or colorants (e.g., to change the color of the as-cooled self-tanning stick).

As described in more detail below, the external solution and the internal solution may be mixed, heated, combined, and mixed further to form an emulsion of the self-tanning composition. The emulsified self-tanning composition may be poured into a mold and cooled to provide a final, stable, DHA-containing, self-tanning stick. The self-tanning stick may be applied to the skin of a user by swiping the stick across the skin. The self-tanning compositions herein remain intact as a solid body when applied—by swiping on skin with pressure. When colorants or dyes are not added, the self-tanning compositions disclosed herein may be substantially opaque or translucent in stick form, may be initially clear when applied to the skin, and may develop to a brown or orange color after a duration (e.g., at least 3 hours). For example, as the DHA reacts with primary and secondary amines and amino acids of skin cells, the DHA provides a brown to orange hue to the skin.

The self-tanning compositions disclosed herein may have a melting point above 50° C., above 60° C., above 70° C., above 80° C., or ranges between any combination of the foregoing values. Upon cooling to below the melting temperature, the self-tanning compositions disclosed herein may form a stable, solid, coherent body. While the self-tanning compositions disclosed herein have demonstrated stability over relatively short durations, the inventors currently believe the self-tanning compositions disclosed herein have a shelf life, under ambient conditions (e.g., 22° C.), of 2 years or more. As used herein, "stable" or derivatives thereof such as "stability" refers to maintaining a solid preformed structure of the water in oil emulsion wherein the active ingredient DHA is also maintained in an active form (e.g., DHA monomer) in the internal phase of the emulsion. While substantially all of the DHA is present in monomer form, it should be understood that some of the dimer form may be present. For example, the DHA monomer may be at least 95 wt % (at least 97 wt %, at least 98 wt %, or at least 99 wt %) of the DHA, with the DHA dimer making up at least some of the remainder of the DHA in the self-tanning composition.

While described as having an internal phase and an external phase, the self-tanning compositions disclosed herein may be alternatively described as a stick or wax having DHA and may include one or more of erythrulose, glycerin, and a solvent (e.g., water) therein. The wax may contain one or more of any of the waxes, gellants, emollients, oils, emulsifiers or other components disclosed herein, in a form that provides at least a semi-solid, stable structure when at room temperature, such as a stick. The DHA may be dissolved in the water and protected (e.g., maintained in monomer form) from any amine or amino groups in the wax. The wax may be stable as disclosed above with respect to maintaining a solid preformed structure where the DHA is maintained in an active form. The DHA, erythrulose, glycerin, and water may be evenly (e.g., homogenously) dispersed throughout the wax. Accordingly, the wax may include a substantially homogenous emulsion of the components (e.g., external phase and internal phase components) disclosed herein.

The wax may include any of the external phase components disclosed herein in any of the amounts disclosed herein. For example, the wax may include one or more individual components (e.g., from the external phase components listed herein) each in an amount of at least 0.1 wt % of the self-tanning composition, such as 0.1 wt % to 50 wt %, 0.25 wt % to 25 wt %, 20 wt % to 50 wt %, 0.5 wt % to 20 wt %, 1 wt % to 10 wt %, 5 wt % to 10 wt %, 5 wt % to 15 wt %, 15 wt % to 25 wt %, 0.25 wt % to 2.0 wt %, 0.5 wt % to 1 wt %, 4 wt % to 10 wt %, 4 wt % to 8 wt %, 3 wt % to 8 wt %, 2 wt % to 8 wt %, 1 wt % to 4 wt %, 1 wt % to 3 wt %, 2 wt % to 5 wt %, 0.5 wt % to 3 wt %, less than 50 wt %, less than 25 wt %, or less than 10 wt % of the self-tanning composition. The wax may be presented as a wax body having or carrying one or more active ingredients therein.

The active ingredients may include one or more of DHA, erythrulose, glycerin, and water. The active ingredients may be present in the wax in an amount of at least 0.1 wt % of the self-tanning composition, such as 0.1 wt % to 50 wt %, 0.25 wt % to 25 wt %, 20 wt % to 50 wt %, 0.5 wt % to 20 wt %, 0.1 wt % to 9 wt %, 1 wt % to 10 wt %, 5 wt % to 10 wt %, 5 wt % to 15 wt %, 15 wt % to 25 wt %, 0.25 wt % to 2.0 wt %, 0.5 wt % to 1 wt %, 4 wt % to 10 wt %, 4 wt % to 8 wt %, 3 wt % to 8 wt %, 2 wt % to 8 wt %, 1 wt % to 4 wt %, 1 wt % to 3 wt %, 2 wt % to 5 wt %, 0.5 wt % to 3 wt %, less than 50 wt %, less than 25 wt %, or less than 10 wt % of the self-tanning composition. For example, the DHA may be present in the wax in an amount that is at least 0.1 wt % of the self-tanning composition, such as 0.1 wt % to 99 wt %, 1 wt % to 20 wt %, 1 wt % to 10 wt %, 5 wt % to 15 wt %, 5 wt % to 10 wt %, less than 20 wt %, less than 10 wt %, or less than 5 wt % of the self-tanning composition.

In examples, the water may be present in the wax as at least 0.1 wt % of the self-tanning composition, such as 1 wt % to 50 wt %, 1 wt % to 10 wt %, 5 wt % to 15 wt %, 10 wt % to 30 wt %, 20 wt % to 50 wt %, at least 9 wt %, at least 15 wt %, less than 50 wt %, or less than 20 wt % of the self-tanning composition. In examples, the erythrulose may be present in the wax as at least 0.1 wt % of the self-tanning composition such as 0.1 wt % to 10 wt %, 0.1 wt % to 3 wt %, 1 wt % to 3 wt %, 3 wt % to 6 wt %, 6 wt % to 10 wt %, less than 5 wt %, or less than 10 wt % of the self-tanning composition. The self-tanning composition may include at least one preservative (e.g., antimicrobial), such as phenoxyethanol, ethylhexylglycerin, or the like. The at least one preservative may be present in the wax as at least 0.1 wt % of the self-tanning composition such as 0.1 wt % to 10 wt %, 0.1 wt % to 2 wt %, 0.5 wt % to 3 wt %, 1 wt % to 3 wt %, 3 wt % to 6 wt %, 6 wt % to 10 wt %, less than 3 wt %, less than 5 wt %, or less than 10 wt % of the self-tanning composition. For example, phenoxyethanol and ethylhexylglycerin may be present in the wax as 0.7 wt % of the self-tanning composition and glycerin may be present in the wax as 5 wt % of the self-tanning composition.

The wax may include or contain additional components of the self-tanning composition, such as any of the internal phase components in any of the amounts thereof described herein. For example, the wax may include dimethyl isosorbide in an amount that is 2 wt % to 5 wt % (e.g., 3 wt %) of the self-tanning composition.

In examples, the self-tanning composition includes a wax containing one or more wax(es) (e.g., any external phase components disclosed herein) suitable for remaining solid and stable at room temperature, 0.1 wt % to 15 wt % DHA (e.g., 10 wt %), at least 0.1 wt % water (e.g., at least 9 wt % or 35 wt %), 0.1 wt % to 10 wt % of at least one glycerin (e.g., 5 wt %), and 0.1 wt % to 9 wt % erythrulose. The DHA is maintained in the wax in an active state, such as by remaining dissolved in water and protected from contact with amine or amino-containing chemical species until application. The self-tanning composition (wax) is stable and solid at room temperatures and above (e.g., up to 50° C. or 60° C.).

The self-tanning compositions disclosed herein may have a final formulation comprising any combination of the relative component amounts disclosed herein. In such examples, the final formulation of the as-formed self-tanning composition may have substantially or identically the same relative composition of components as are combined together to form the composition. In some examples, the final formulation of the as-formed self-tanning composition may have a different relative composition of components than the relative amounts that were originally combined together. For example, at least some solvent may be driven off of the internal phase and/or external phase during heating. In either case, it is understood that the final composition of the as-formed self-tanning composition flows from the methods disclosed herein.

FIG. 1 is a schematic of a method 10 of making and using a solid self-tanning composition containing DHA. The method 10 includes an act 12 of forming the external phase 100, an act 14 of forming the internal phase 200, an act 16 of combining the external phase 100 with the internal phase 200 to form a self-tanning composition, an act 18 of placing the self-tanning composition in a mold 400, an act 20 of cooling the self-tanning composition to form a self-tanning stick 500; and an act 22 of applying the self-tanning composition of the self-tanning stick to the skin of a person. In some examples, one or more of the acts 12-22 may be omitted, carried out in another order than is presented, or may be combined with any other act. For example, the method 10 may only include forming the self-tanning composition (e.g., acts 12-16), only forming the self-tanning stick (e.g., acts 12-20), or only using the self-tanning stick (e.g., act 22). Further acts may be carried out in the method 10, such as placing the self-tanning stick(s) in packaging or application vessels.

The act 12 of forming the external phase 100, may include forming the external phase 100 with one or more of any of the external phase components disclosed herein in any of the amounts disclosed herein. Forming the external phase 100 may include adding each of the one or more external phase components to a vessel and applying heat to the vessel. In some examples, forming the external phase 100 may include heating at least some of the one or more external phase components (e.g., in separate vessels) then adding the same to a single vessel while heating the vessel. Forming the external phase 100 may include heating one or more of the external phase components while mixing the external phase components. For example, heating the one or more of the external phase components may include heating the external phase components above a melting temperature of the one or more external phase components, such as to a temperature of at least 50° C., at least 70° C., at least 70° C., at least 80° C., at least 85° C., at least 90° C., at least 100° C., less than 150° C., less than 125° C., or less than 120° C., or ranges between any combination of the foregoing values as endpoints (e.g., 80° C. to 90° C.).

The external phase components may be placed (e.g., poured) into the vessel and may be mixed together to form a substantially homogenous mixture, such as an emulsion or liquid. Forming the external phase 100 may include mechanically mixing the components of the external phase such as by a one or more of a propeller mixer, a stir bar, a stir plate, a paddle mixer, or the like. The external phase may be simultaneously mixed and heated. For example, heat may be applied to a mixing vessel containing the external phase components. The heat applied to the vessel may be sufficient to (heat to and) maintain the external phase components at a selected temperature, such as any of the temperatures disclosed above.

In an example, the external phase may be formed by adding synthetic wax, *Euphorbia cerifera* (candelilla) wax, ozokerite, neopentyl glycol diethylhexanoate, isononyl isononanoate, isosorbide dicaprylate, dimethicone, dimethicone/polyglycerin-3 crosspolymer dimethicone, and peg-9 polydimethylsiloxyethyl dimethicone to a vessel. The vessel may be heated to a temperature of 80° C. to 90° C. and a propeller mixer may mix the external phase components as they melt. The external phase is mixed and heated until a substantially homogenous fluid is formed. The fluid should contain substantially no solids.

The relative amounts of the external phase components (e.g., as a weight percentage of the self-tanning composition) in the example may be 4 wt % to 10 wt % (e.g., 8 wt %) synthetic wax, 0.25 wt % to 2 wt % (e.g., 1 wt %) *Euphorbia cerifera* (candelilla) wax, 4 wt % to 10 wt % (e.g., 6 wt %) ozokerite, 4 wt % to 8 wt % (e.g., 6 wt %) neopentyl glycol diethylhexanoate, 4 wt % to 8 wt % (e.g., 6 wt %) isononyl isononanoate, 1 wt % to 4 wt % (e.g., 3 wt %) isosorbide dicaprylate, 2 wt % to 8 wt % (e.g., 5 wt %) dimethicone, 4 wt % to 8 wt % (e.g., 6 wt %) dimethicone/polyglycerin-3 crosspolymer dimethicone, and 0.5 wt % to 3 wt % (e.g., 2 wt %) PEG-9 polydimethylsiloxyethyl dimethicone.

The synthetic wax may act as a wax gellant. The *Euphorbia cerifera* (candelilla) wax may act as a wax gellant. The ozokerite may act as a wax gellant. The neopentyl glycol diethylhexanoate may act as an emollient. The isononyl isononanoate may act as an emollient. The isosorbide dicaprylate may act as an emollient and skin penetration enhancer. The dimethicone may act as an emollient base. The dimethicone/polyglycerin-3 crosspolymer dimethicone may act as an emulsifier. The PEG-9 polydimethylsiloxyethyl dimethicone may act as an emulsifier.

Further embodiments with different external phase components and/or amounts thereof than those in the above example are considered, and some are discussed below in the working examples. Further, the external phase may be formed and provided in more than one part, such as having a two part (or more) external phase, where each of parts are combined into the internal phase sequentially. Each part of the multipart external phase may include one or more of the external phase components disclosed herein.

In some examples, the act 14 of forming the internal phase 200, may include forming the internal phase 200 with one or more of any of the internal phase components disclosed herein in any of the amounts disclosed herein. Forming the internal phase 200 may include adding each of the one or more internal phase components to a vessel and applying heat to the vessel. In some examples, forming the internal phase 200 may include heating at least some of the one or more internal phase components (e.g., in separate vessel(s)) then adding the same to a single vessel while heating the vessel. Forming the internal phase 200 may include heating one or more of the internal phase components while mixing the internal phase components. For example, heating the one or more of the internal phase components may include heating the internal phase components above a melting temperature of the one or more internal phase components, such as to a temperature of at least 50° C., at least 70° C., at least 70° C., at least 80° C., at least 85° C., at least 90° C., at least 100° C., less than 150° C., less than 125° C., or less than 120° C., or ranges between any combination of the foregoing values as endpoints (e.g., 85° C. to 90° C.).

The internal phase components may be placed (e.g., poured) into the vessel and may be mixed together to form a substantially homogenous mixture, such as a solution or emulsion. Forming the internal phase 200 may include mechanically mixing the components of the internal phase such as by a one or more of a propeller mixer, a stir bar, a stir plate, a paddle mixer, or the like. The internal phase may be simultaneously mixed and heated. For example, heat may be applied to a mixing vessel containing the internal phase components. The heat applied to the vessel may be sufficient to (heat to and) maintain the internal phase components at a selected temperature, such as any of the temperatures disclosed above.

In an example, the internal phase may be formed by adding water, phenoxyethanol, ethylhexylglycerin, dimethyl isosorbide, erythrulose, glycerin, and DHA to a vessel. The vessel may be heated to a temperature of 60° C. to 150° C. (e.g., 85° C. to 120° C.) and a propeller mixer may mix the internal phase components as they melt. The internal phase 200 is mixed and heated until a substantially homogenous fluid is formed. The fluid should contain substantially no solids. All of the DHA should be dissolved in the internal phase 200.

The relative amounts of the internal phase components (e.g., as a weight percentage the self-tanning composition) in the example may be 0.1 wt % to 70 wt % (e.g., 20 wt % to 50 wt % or 36 wt %) water, 0.5 wt % to 2 wt % (e.g., 1 wt %) phenoxyethanol and ethylhexylglycerin, 2 wt % to 5 wt % (e.g., 3 wt %) dimethyl isosorbide, 1 wt % to 3 wt % (e.g., 2 wt %) erythrulose, 3 wt % to 8 wt % (e.g., 5 wt %) glycerin, and 5 wt % to 15 wt % (e.g., 10 wt %) DHA.

The water acts as a solvent. The phenoxyethanol and ethylhexylglycerin may act as preservatives (e.g., anti-microbials). The dimethyl isosorbide may act as a skin penetration enhancer. Erythrulose may act as a DHA color modifier/enhancer. The glycerin may act as a solvent, humectant, and moisturizer. The DHA acts as a self-tanning agent/colorant.

Further embodiments with different internal phase components and/or amounts thereof than those in the above example are considered, and some are discussed below in the working examples. Further, the internal phase may be formed and provided in more than one part, such as having a two part (or more) internal phase, where each of the parts are combined sequentially to form the internal phase. Each part of the multipart internal phase may include one or more of the internal phase components disclosed herein.

In some examples, the act 16 of combining the external phase 100 with the internal phase 200 to form a self-tanning composition may include adding the internal phase 200 into the external phase 100 or vice versa. The internal phase 200 may be added to the external phase 100 in one or more aliquots, such as steadily pouring the internal phase 200 into the external phase 100 in one or more portions. In such examples, the portions may be identical or different in one or more of composition or amount.

The act 16 of combining the external phase 100 with the internal phase 200 to form a self-tanning composition 300 may include heating to and/or maintaining the self-tanning composition 300 (e.g., combined internal and external phases) at a selected temperature. In such examples, heating/maintaining the temperature of the self-tanning composition 300 may include maintaining the self-tanning composition 300 at a selected temperature. The selected temperature may be above the melting point of all components of the self-tanning composition 300, such as at least 50° C., at least 60° C., at least 70° C., at least 80° C., at least 85° C., at least 90° C., at least 100° C., less than 150° C., less than 125° C., or less than 120° C., or ranges between any combination of the foregoing values as endpoints (e.g., 80° C. to 90° C., 85° C. to 90° C., or 90° C. to 100° C.). As noted above, the internal and external phases may be at relatively similar temperatures prior to combination. By heating the internal phase 200 to a similar temperature (e.g., within 15° C., within 10° C., or within 5° C.) as the external phase 100, the internal and external phases may more readily form an emulsion (the self-tanning composition 300) than when the temperature difference is relatively large.

In examples, the external phase components may be placed (e.g., poured, aliquoted, etc.) in the vessel containing the internal phase components and may be mixed together to form a substantially homogenous mixture, such as an emulsion of the self-tanning composition 300. The self-tanning composition 300 includes the internal phase containing DHA in an amount that is greater than 0.1 wt % and water in an amount that is greater than 9 wt % of the self-tanning composition. The internal phase is contained within the external phase of the self-tanning composition 300. While described as an emulsion and homogenous mixture, it should be understood that in some examples, the internal phase may be mixed in the external phase in mixtures that are not homogenous and may not be emulsions. Any mixture of the internal phase and internal phase components may be utilized so long as the DHA is maintained in monomeric form.

The act 16 of combining the external phase 100 with the internal phase 200 to form a self-tanning composition 300 may include mechanically mixing the components of the internal phase 200 with the components of the external phase 100 such as by a one or more of a propeller mixer, a stir bar, a stir plate, a paddle mixer, or the like. The act 16 of combining the external phase 100 with the internal phase 200 to form a self-tanning composition 300 may include homogenizing the self-tanning composition 300 (e.g., forming a substantially homogenous emulsion of internal phase and external phase) such as by any of the mixing techniques disclosed herein. The act 16 of combining the external phase 100 with the internal phase 200 to form a self-tanning composition 300 may include mixing the external phase 100 with the internal phase 200 in a continuous pour line where the components are poured together, such as prior to or by pouring the components together. The components may be further mixed after pouring such as via any of the mechanical mixing techniques disclosed herein. The self-tanning composition 300 may be simultaneously mixed and heated. For example, heat may be applied to a mixing vessel containing the mixture of the internal phase and external phase.

The act 16 of combining the external phase 100 with the internal phase 200 to form a self-tanning composition 300 may include maintaining the mixture (e.g., emulsion) of the internal phase and external phase at the selected temperature.

In examples, the act 18 of placing the self-tanning composition in a mold 400 may include pouring the self-tanning composition 300 into the mold 400. The mold 400 may include one or more cavities therein, sized and spaced to form one or more distinct bodies of the self-tanning composition 300 (e.g., self-tanning sticks 500) upon cooling. For example, the mold 400 may include one or more individual packages or housings for forming an individual stick. In such examples, the mold 400 may include a roll-on or roll-up stick package (e.g., application vessel) similar or identical to those used for a deodorant stick. Such packages may include screws, slides, levers, or other means of advancing the self-tanning stick in the packaging to make more of the self-tanning stick available for use as the self-tanning stick is applied. In examples, placing the self-tanning composition 300 in a mold 400 may include injecting, aliquoting, ladling, etc., the self-tanning composition 300 into the mold 400. The act 18 of placing the self-tanning composition 300 in a mold 400 may at be carried out at or near the selected temperature, such as at a temperature greater than the melting point of all materials in the self-tanning composition 300.

The act 20 of cooling the self-tanning composition 300 to form a self-tanning stick 500 may include allowing the self-tanning composition 300 to cool to ambient temperature by removing all heat sources from the self-tanning composition 300 or container (e.g., mold) holding the same. In examples, cooling the self-tanning composition 300 to form a self-tanning stick 500 may include disposing the mold 400 in a fluid bath having a temperature below the melting temperature of some or all components of the self-tanning composition 300. For example, cooling the self-tanning composition 300 to form a self-tanning stick 500 may include disposing the mold 400 in a freezer, refrigerator, blower, cooling tunnel, water bath, etc. to lower the temperature of the self-tanning composition 300 to below the melting temperature of some or all components of the self-tanning composition 300. Upon cooling the self-tanning composition 300 to below the melting temperature of some or all components of the self-tanning composition 300 the internal phase 200 may be trapped in place by the external phase to form the solid self-tanning stick 500.

The self-tanning stick 500 may include any combination of internal and external phase components in emulsion form, wherein the emulsion is a water in oil emulsion having at least 0.1 wt % DHA and at least 1 wt % water (e.g., at least 9 wt % water). The self-tanning stick 500 may alternatively be described as a wax body having a substantially homogenous mixture of components (e.g., active components and waxes). The self-tanning sticks 500 are stable in temperatures up to 60° C. and are stable at ambient temperatures for at least 2 years.

In some examples, the self-tanning stick 500 may be similar or identical in shape and appearance to a deodorant stick. The self-tanning stick 500 may be used to apply the self-tanning composition containing the DHA directly onto the skin of a user.

It should be understood that the vessels and quantities of components disclosed herein may vary, such as from benchtop/lab scale to industrial scale. For example, the quantities of components may be used in a continuous pour line where the components are mixed, heated, and cooled in a continuous line.

In some embodiments, an act of providing the self-tanning composition (e.g., in self-tanning stick form) may be included in the method 10. Providing a self-tanning stick may include any of the acts 12-20 or may include purchasing or otherwise procuring the self-tanning stick 500. The self-tanning composition 300 may be applied to the skin of a person either directly or indirectly.

The act 22 of applying the self-tanning composition 300 of the self-tanning stick 500 to the skin of a person 600 may include swiping the self-tanning stick 500 across one or more portions of the skin of the person 600 at a pressure sufficient to ensure at least some of the self-tanning composition remains on the person's 600 skin (e.g., as a thin film). In some examples, applying the self-tanning composition 300 of the self-tanning stick 500 to the skin of a person 600 may include substantially evenly coating one or more body parts (e.g., arms, legs, etc.) with the self-tanning composition 300. As the self-tanning composition 300 remains on the skin, any skin penetration aids therein may aid the DHA in accessing amine or amino groups in the skin cells (e.g., in or under the stratum corneum) of the user. The DHA may bond to the amine or amino groups on the skin cells and provide a brown to orange hue to the skin of the user. The color provided by the DHA depends upon the pH of the self-tanning composition 300.

WORKING EXAMPLES

Various working examples were formed according to the methods and compositions disclosed above. All weight percentages listed below are provided as the weight percent of the total weight of the respective self-tanning composition (e.g., all external phases and internal phases combined).

Working Example 1

Working example 1 was formed according to the following procedure. A first external phase included 3 wt % isosorbide dicaprylate (HydraSynol DOI), 12 wt % isodecyl neopentanoate (Bernel Ester 105 from Alzo), 14.2 wt % isohexadecane (Fancol IH-CG from Fancor), 21 wt % sorbitan oleate (Tego SMO V from Evonik), 3.7 wt % dibutyl lauroyl glutamide (gelling agent GP-1 from Ajinomoto OmniChem of Belgium), and 2.5 wt % dibutyl ethylhexanoyl glutamide (gelling agent EB-21 from Ajinomoto OmniChem of Belgium). The first external phase was combined, heated to 125° C., and mixed under mechanical agitation until all components were melted and in solution.

The following external phase components were added to the first external phase sequentially and mixed until liquid to form the second external phase. First, 0.5 wt % Bisabolol (Dragosantol® 100) was added, then 0.7 wt % vitamin E acetate (e.g., dl-alpha-tocopheryl acetate from Ashland- Adisseo), 4.3 wt % polysorbate 80 (from Univar), 0.5 wt % chamomile abstract (e.g., actiphyte of chamomile from Active Organics), and 2.5 wt % hydroxyl stearic acid (Kester wax K-60P Wax #484B from Brenntag Specialties, Inc.). The components of the second external phase were heated and mixed under mechanical agitation until a homogenous solution was observed. The temperature of the second external phase was then lowered to 85° C. and maintained.

The internal phase was formed separately from the external phases. The internal phase included 9 wt % water, 0.1 wt % aloe vera powder 200:1 concentration, 4 wt % glycerin (glycerine 99.7% USP Kosher 917), 15 wt % DHA (from EMD), and 7 wt % erythrulose. The internal phase components were combined, heated to 40° C., and mixed under mechanical agitation until a homogenous solution was observed.

The second external phase was then added to the internal phase to form the composition of working example 1. The phases were mixed at a high speed until substantially homogenous. The heat of the mixture containing internal and external phases was maintained at 85° C.

The cooled mixture formed a self-tanning stick containing 9 wt % water, 15 wt % DHA and remained a solid coherent body.

Working Example 2

Working example 2 was formed according to the following procedure. A first external phase included 3 wt % isosorbide dicaprylate (HydraSynol DOI), 7 wt % cyclomethicone (Dow Corning 345 from Dow), 0.5 wt % L-Bisabolol (Dragosantol® 100), 3.7 wt % dibutyl lauroyl glutamide (gelling agent GP-1 from Ajinomoto OmniChem of Belgium), 2.5 wt % dibutyl ethylhexanoyl glutamide (gelling agent EB-21 from Ajinomoto OmniChem of Belgium), 21 wt % sorbitan oleate (Tego SMO V from Evonik), 4.3 wt % polysorbate 80 (from Univar), 2.5 wt % hydroxyl stearic acid (Kester wax K-60P Wax #484B from Brenntag Specialties, Inc.), and 0.7 wt % vitamin E acetate (e.g., dl-alpha-tocopheryl acetate from Ashland-Adisseo). The first external phase was combined, heated to 135° C., and mixed under mechanical agitation until all components were melted and in solution. Then the first external phase was cooled to, and maintained at, 115° C.

The internal phase was formed separately from the first external phase. The internal phase included 9 wt % water (deionized water), 0.1 wt % aloe vera powder 200:1 concentration, 4 wt % glycerin (glycerine 99.7% USP Kosher 917), 15 wt % DHA (from EMD), and 7 wt % erythrulose. The internal phase components were mechanically mixed with a mixer at room temperature until a homogenous solution was observed.

The heat to the first external phase was terminated. The internal phase was poured into the first external phase and mixed under mechanical agitation at high speed until a homogenous solution of the intermediate mixture was observed. The temperature of the intermediate mixture was maintained at 80° C.

The following additional external phase components were added to the intermediate mixture and mixed until in liquid phase to form the composition of working example 2, as follows. The additional external phase components included 14.2 wt % isohexadecane (Fancol IH-CG from Fancor), 5 wt % cyclopentasiloxane (DC 245 fluid from Dow), and 0.5 wt % chamomile abstract (e.g., actiphyte of chamomile from Active Organics) and were added to the intermediate mixture to form the composition of working example 2. Working example 2 was mixed until a homogenous solution was observed while the heat was maintained at 80° C.

The cooled mixture formed a self-tanning stick containing 9 wt % water, 15 wt % DHA and remained a solid coherent body.

Working Example 3

Working example 3 was formed according to the following procedure. An external phase and an internal phase were formed.

The external phase included 8 wt % synthetic wax, 1 wt % *Euphorbia cerifera* (candelilla) wax, 6 wt % ozokerite, 6 wt % neopentyl glycol diethylhexanoate, 6 wt % isononyl isononanoate, 3 wt % isosorbide dicaprylate, 5 wt % dimethicone, 6 wt % dimethicone/polyglycerin-3 crosspolymer dimethicone, and 2 wt % PEG-9 polydimethylsiloxyethyl dimethicone. The components of the external phase were placed into a propeller mixer. The components of the external phase were heated to 80° C. to 90° C. while being mixed. The mixture was mixed until all components were melted and a substantially homogenous appearance was observed.

The internal phase included 36.3 wt % water, 0.7 wt % phenoxyethanol and ethylhexylglycerin, 3 wt % dimethyl isosorbide, 2 wt % erythrulose, 5 wt % glycerin, and 10 wt % DHA (in powder form). The components of the internal phase were placed into a propeller mixer. The internal phase components were mixed under mechanical agitation until all components were in solution and a substantially homogenous appearance was observed. The internal phase components were slowly heated to 85° C. to 90° C.

The internal phase materials were slowly poured into the external phase materials while being maintained at 85° C. to 90° C. and subjected to propeller mixing for 45 minutes after all of the internal phase was added to the external phase. The mixture formed the composition of working example 3. Working example 3 progressively grew more opaque and thicker with the addition of the internal phase. Working example 3 was an emulsion of the internal and external phases.

The mixture (Working example 3) was then poured into a mold and moved through a cooling tunnel. The cooled mixture formed a self-tanning stick containing 36.3 wt % water, 10 wt % DHA, and remained a solid coherent body. The self-tanning stick was a substantially white solid.

The self-tanning stick of working example 3 rubbed on the skin of a person in a clear film. The clear film slowly developed a brown hue on the person's skin over a period of a few hours.

In some examples, any of the self-tanning compositions disclosed herein may be formed, disposed in a self-tanning stick or other form, or may be applied to the skin of a person.

While various aspects and embodiments have been disclosed herein, other aspects and embodiments are contemplated. The various aspects and embodiments disclosed herein are for purposes of illustration and are not intended to be limiting.

What is claimed is:

1. A self-tanning composition, comprising:
   a solid body in stick form including a water in oil emulsion, the water in oil emulsion including:
   an external phase including waxes and one or more of gellants, emollients, emulsifiers, or skin penetration enhancers, wherein the waxes are 10 wt % to 25 wt % of the water in oil emulsion; and
   an internal phase including water and dihydroxyacetone in monomer form;

wherein the water is 25 wt % to 50 wt % of the water in oil emulsion, dihydroxyacetone is 8 wt % to 15 wt % of the water in oil emulsion, and the solid body is stable at ambient temperatures.

2. The self-tanning composition of claim 1, wherein the water is 25 wt % to 40 wt % of the water in oil emulsion.

3. The self-tanning composition of claim 1, wherein the water is 30 wt % to 40 wt % of the water in oil emulsion.

4. The self-tanning composition of claim 1, wherein the water is 30 wt % to 50 wt % of the water in oil emulsion.

5. The self-tanning composition of claim 1, wherein the dihydroxyacetone is 8 wt % to 10 wt % of the water in oil emulsion.

6. The self-tanning composition of claim 1, wherein the dihydroxyacetone is 10 wt % to 15 wt % of the water in oil emulsion.

7. The self-tanning composition of claim 1, wherein:
the water is 25 wt % to 40 wt % of the water in oil emulsion; and
the dihydroxyacetone is 10 wt % to 15 wt % of the water in oil emulsion.

8. The self-tanning composition of claim 1, wherein the internal phase includes:
30 wt % to 40 wt % water; and
one or more of 0.5 wt % to 2 wt % of at least one preservative, 2 wt % to 5 wt % dimethyl isosorbide, 1 wt % to 3 wt % erythrulose, and 3 wt % to 8 wt % glycerin.

9. The self-tanning composition of claim 1, wherein the internal phase has a pH of 3 to 7.

10. A self-tanning composition comprising:
a wax body including 8 wt % to 15 wt % dihydroxyacetone, 10 wt % to 25 wt % wax, and 25 wt % to 50 wt % solvent therein, the wax body being in solid stick form;
wherein the dihydroxyacetone is dissolved in the solvent and maintained in monomer form in the solvent within the wax body.

11. The self-tanning composition of claim 10, further comprising 0.1 wt % to 10 wt % of at least one glycerin and 0.1 wt % to 9 wt % erythrulose therein.

12. The self-tanning composition of claim 10, wherein the wax body includes one or more of synthetic wax, *Euphorbia cerifera* (candelilla) wax, ozokerite, neopentyl glycol diethylhexanoate, isononyl isononanoate, isosorbide dicaprylate, dimethicone, dimethicone/polyglycerin-3 crosspolymer dimethicone, or PEG-9 polydimethylsiloxyethyl dimethicone, a gellant, or paraffin wax therein.

13. The self-tanning composition of claim 10, wherein the dihydroxyacetone and solvent are dispersed substantially homogenously throughout the wax body.

14. The self-tanning composition of claim 10, wherein the solvent includes one or more of water or propylene glycol.

* * * * *